(12) United States Patent
Marion et al.

(10) Patent No.: US 6,547,933 B2
(45) Date of Patent: Apr. 15, 2003

(54) PROCESS FOR THE PURIFICATION OF AROMATIC POLYAMINES

(76) Inventors: Philippe Marion, 140, route de Buye, F-69 390 Vernaison (FR); Stephane Montarsolo, 34, avenue Villemain, F-75 014 Paris (FR)

( * ) Notice: Subject to any disclaimer, the term of this patent is extended or adjusted under 35 U.S.C. 154(b) by 0 days.

(21) Appl. No.: 10/116,251

(22) Filed: Apr. 4, 2002

(65) Prior Publication Data

US 2002/0108845 A1 Aug. 15, 2002

Related U.S. Application Data

(63) Continuation of application No. 09/294,153, filed on Apr. 19, 1999, now abandoned.

(30) Foreign Application Priority Data

Apr. 17, 1998 (FR) .............................. 98 04839

(51) Int. Cl.[7] .............................. B01D 1/00; B01D 3/00; C07C 209/84; C07C 209/86
(52) U.S. Cl. ..................... 203/78; 159/47.1; 159/901; 203/94; 203/98; 203/99; 203/DIG. 9; 203/DIG. 19; 564/424; 564/437
(58) Field of Search ..................... 203/73, 78, DIG. 9, 203/99, DIG. 19, 94, 98; 564/424, 437; 159/47.1, 901

(56) References Cited

U.S. PATENT DOCUMENTS

| | | | |
|---|---|---|---|
| 3,420,752 A | 1/1969 | Kirss | 203/94 |
| 3,647,054 A | 3/1972 | Tsuboi | 203/29 |
| 4,131,622 A | 12/1978 | Popoff | 260/576 |
| 5,684,180 A * | 11/1997 | Knofel et al. | 564/347 |
| 5,714,634 A | 2/1998 | Casale | 564/422 |
| 5,728,880 A | 3/1998 | Beckhaus | 564/305 |
| 6,359,177 B1 * | 3/2002 | Brady et al. | 564/424 |

FOREIGN PATENT DOCUMENTS

WO    WO 94/06752    3/1994

* cited by examiner

Primary Examiner—Virginia Manoharan

(57) ABSTRACT

A process for the purification of a mixture of aromatic polyamines obtained by hydrogenation of the corresponding aromatic polynitro compounds, said mixture including the various isomers of the said amines as well as reaction by-products, including the steps of carrying out a distillation of the mixture in a distillation column, wherein a first stream, corresponding to a fraction or to all of the stream recovered at the bottom of the distillation column, is separated and is used in a chemical reaction and a second stream is separated corresponding (i) to a stream drawn off from the side in the gas phase, in the lower third of the said column, this stream representing at most 20% or more than 80% of the total volume (first and second stream); or (ii) to a fraction of the first stream, this fraction representing 2 to 50% of the volume of the first stream; in order to treat it subsequently.

11 Claims, 1 Drawing Sheet

PROCESS FOR THE PURIFICATION OF AROMATIC POLYAMINES

This application is a Continuation application of application Ser. No. 09/294,153 filed on Apr. 19, 1999 now abandoned.

BACKGROUND OF THE INVENTION

The subject-matter of the present invention is a process for the purification of aromatic polyamines obtained by hydrogenation of the corresponding aromatic polynitro compounds.

It is well known that the products resulting from the hydrogenation reaction of aromatic polynitro compounds comprise a mixture of the various isomers of the polyamino compounds, as well as volatile by-products and by-products with a high boiling point (also referred to (herein)below as heavy by-products).

Thus, it is clearly necessary, on the one hand, to separate the aromatic polyamino compounds from the by-products but, on the other hand, it can prove to be important to separate certain isomers of these polyamines from the others, as not all are equally advantageous in subsequent applications.

Such a situation is found during the synthesis of toluenediamine (TDA), which comprises two types of isomers, the ortho and meta isomers, of which only the two meta isomers are of advantage, essentially in the production of toluene diisocyanate. In addition, the reaction mixture resulting from the hydrogenation reaction comprises volatile by-products, such as toluidine, for example, as well as heavy by-products.

It is known in the art to treat the reaction mixture resulting from the hydrogenation reaction of the corresponding aromatic dinitro compounds by distillation, after having carried out preliminary stages of dehydration of the reaction mixture and optionally of removal of the solvent, if it had been present during the hydrogenation reaction. The volatile by-products as well as the ortho-TDA isomers (2,3-TDA, 3,4-TDA) are recovered at the top of this distillation column; the heavy by-products comprising meta-TDA are recovered at the column bottom. The amount of heavy by-products can represent from 0.1 to 2.5% by weight of the recovered mixture.

The mixture of heavy by-products and of meta-TDA is then treated so as to evaporate all the meta-TDA present. However, this process is the cause of a loss in meta-TDA, which is trapped in the heavy by-products. This amount can represent 25 to 200% by weight of the heavy compounds.

The problem which is therefore not solved in a completely satisfactory way by the conventional processes is therefore to separate the meta-TDA isomers from these heavy by-products while losing the minimum possible amounts of these isomers.

With the aim of limiting the losses of this compound, Patent Application WO 94/006752 has provided for the separation of the meta-TDA from the heavy by-products by distilling this mixture in the presence of a third solvent with a boiling point greater than 290° C. While this process makes it possible to limit the losses of the desired product in the heavy by-products, it requires, however, the use of a third compound, which increases the cost, as well as the installation of new equipment.

In German Patent DE 196 08 443, the solution recommended consists of an arrangement comprising the conventional vacuum distillation column and evaporators. More particularly, the mixture of polyamines is introduced into the vacuum distillation column, from which column is recovered, at the top, a mixture of light by-products, as well as the isomers of ortho-TDA. At the column bottom, all the stream, comprising the meta-TDA as well as the heavy by-products, is conveyed into an evaporator, where it is evaporated. The evaporated fraction is condensed and stored or used in a subsequent chemical reaction. The non-evaporated fraction is mixed with a stream drawn off from the side in the upper half of the distillation column and then evaporated in its turn. The products remaining liquid are separated, in order to be destroyed, for example; as for the evaporated fraction, it is returned to the distillation column. An alternative form of this arrangement consists in feeding the distillation column not with the mixture of TDA and of by-products but with the evaporated fraction of this mixture. The non-evaporated fraction is treated in the same way as the non-evaporated stream collected after the evaporation of the stream recovered at the column bottom in the preceding alternative form. The purified meta-TDA is then recovered at the bottom of the distillation column.

This document discloses a process which makes it possible to decrease the losses of meta-TDA present in the heavy by-products without, however, eliminating them. However, this process is complex and requires the installation of many items of equipment.

BRIEF SUMMARY OF THE INVENTION

The aim of the present invention is to provide a simple and efficient process for the purification of a mixture of aromatic polyamines which does not require the installation of numerous expensive devices, without loss of aromatic polyamines.

These aims and others are achieved by the present invention, the subject-matter of which is therefore a process for the purification of a mixture of aromatic polyamines which are obtained by hydrogenation of the corresponding aromatic polynitro compounds, which mixture comprises the various isomers of the said amines as well as reaction by-products. The process according to the invention consists in carrying out a distillation of the said mixture and in then carrying out the following operations:

a first stream, corresponding to a fraction or to all of the stream recovered at the bottom of the distillation column, is separated and is used in a chemical reaction (such as phosgenation, for example), a second stream is separated corresponding:
(i) to a stream drawn off from the side in the gas phase, in the lower third of the said column, this stream representing at most 20% or more than 80% of the total volume (first and second stream); or
(ii) to a fraction of the first stream, this fraction representing 10 to 50% of the volume of the first stream, in order to treat it subsequently.

The process according to the present invention therefore makes it possible to obtain desired polyamine isomers (meta isomers, in the case of TDA) which are devoid of heavy by-products, without loss of polyamines. This is because the unpurified fraction (comprising the meta isomers and the heavy by-products) is advantageously recycled in a subsequent reaction, such as phosgenation.

It should be noted that such a procedure was not obvious per se because the "recycled" mixture must exhibit a suitable ratio of desired isomers. For example, in the case of the meta isomers of toluenediamine, the 2,4/2,6 isomeric ratio must be between 3.6 and 4.2.

Thus, the process according to the invention makes it possible simultaneously to obtain, and in respective proportions which can be adjusted to a certain extent and according to market requirements, for example, a mixture comprising the isomers and the heavy by-products and, on the other hand, isomers devoid of heavy by-products (lightened polyamine).

Furthermore, the process according to the invention for the separation of the desired isomers from the heavy by-products is efficient because the purity of desired isomers is at least 99% and advantageously greater than or equal to 99.5%.

These aims and others will become more clearly apparent on reading the description and appended figures which will follow.

Figure 1:
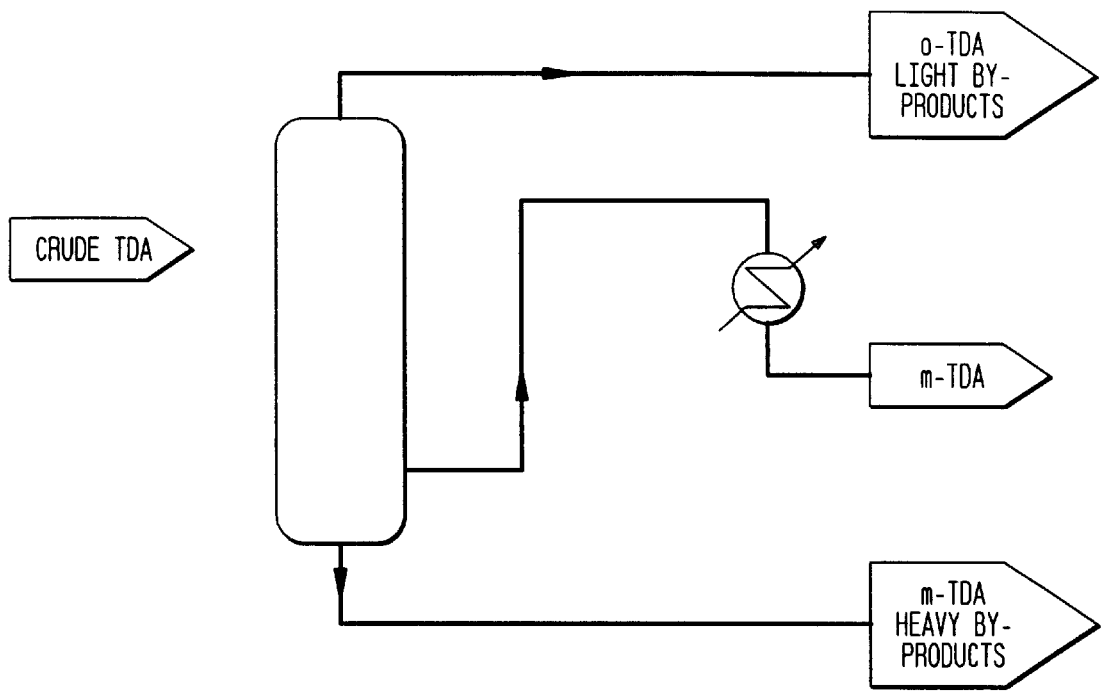
FIG. 1 represents a first embodiment of a process according to the invention.

FIG. 1 represents a first alternative form, in which a side gas stream (corresponding to the second stream (i)) is drawn off from the distillation column and then introduced into a condenser, so as to obtain the desired meta isomers devoid of heavy by-products. At the bottom of this column, a stream (corresponding to the first stream) is recovered comprising the same desired isomers with the heavy by-products. This stream is advantageously used in a chemical reaction without further purification treatment.

Figure 2:
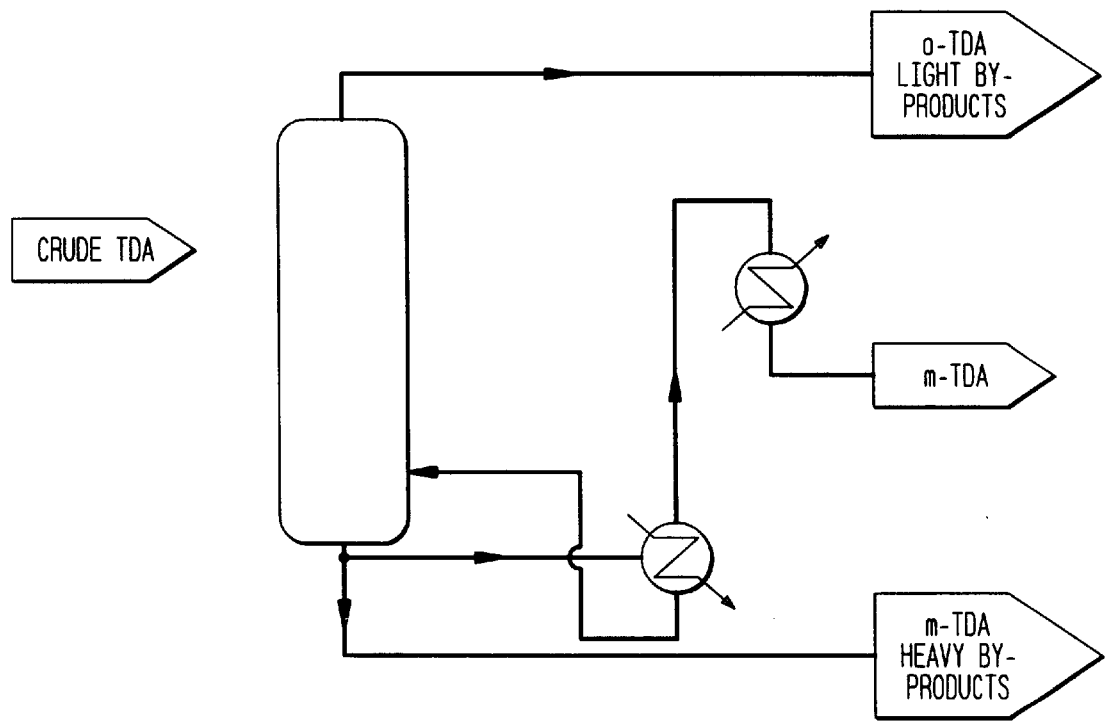
FIG. 2 represents a second embodiment of a process according to the invention.

FIG. 2 represents the second alternative form, in which a fraction of the first stream (corresponding to the second stream (ii)) is conveyed to an evaporator, in order to be partially evaporated therein. The fraction remaining liquid is returned to the distillation column at the level of the bottom quarter of the latter. The evaporated fraction, comprising the desired isomer, is condensed and stored.

Before describing the process according to the invention in detail, the aromatic polyamines treated will be defined.

Thus, the term "aromatic polyamine" is understood to mean any compound comprising at least two primary amine functional groups and at least one $C_6$–$C_{14}$, preferably $C_6$–$C_{10}$, aromatic unit which may or may not be substituted by one or more saturated or unsaturated, linear, cyclic or branched, $C_1$–$C_{10}$ hydrocarbon-comprising radicals.

More specifically, the abovementioned hydrocarbon-comprising radicals, optionally substituting the said aromatic units, can be chosen from $C_1$–$C_{10}$, preferably $C_1$–$C_6$, alkyl, aryl, alkylaryl and arylalkyl radicals.

The term "aromatic polyamine" is preferably understood to mean a compound of formula: $H_2N$—R—$NH_2$, in which formula R represents the substituted or unsubstituted aromatic unit described above.

According to a more specific embodiment of the invention, the abovementioned unit R is optionally substituted by one or more $C_1$–$C_{10}$, preferably $C_1$–$C_6$, alkyl radicals. Mention may in particular be made, by way of example, of the benzene and naphthalene nuclei which may or may not be substituted by one or more methyl, ethyl, propyl, butyl, pentyl or hexyl radicals and/or their isomers.

The aromatic polyamine is preferably chosen from toluenediamine and its isomers, xylenediamine and its isomers, or phenylenediamine and its isomers.

As was indicated previously, the said aromatic polyamines are obtained by hydrogenation of the corresponding aromatic polynitro compounds, the is formula for which is as follows: $O_2N$—R—$NO_2$, in which formula R has the same definition as above.

The hydrogenation of the nitro compounds is entirely conventional in the field.

It is carried out by employing a catalyst, which is dispersed in the reaction mixture. The latter is separated at the end of the reaction by filtration, in particular.

It should be noted that the hydrogenation reaction may or may not be carried out in the presence of a solvent which is inert under the reaction conditions. Mention may be made, among conventional solvents, of alcohols exhibiting a low boiling point, such as methanol, ethanol or isopropanol, or alternatively of ethers, such as tetrahydrofuran.

The reaction mixture resulting from the hydrogenation comprises the various isomers of the polyamino compounds, heavy and volatile by-products, as well as water, and, if appropriate, the solvent.

Use is conventionally made of a preliminary stage of separation of the solvent, in the case where the latter is present, and then of the water produced during the reaction.

These operations are entirely standard in the field and are generally carried out by distillation of the reaction mixture.

In all which will follow, and for reasons of simplification of the account, reference will be made only to toluenediamine, to its ortho and meta isomers and to the heavy and volatile by-products obtained during the hydrogenation of dinitrotoluenes, it being known that the process according to the invention can be employed for the purification of other mixtures of polyamines obtained by hydrogenation of the corresponding polynitro compounds.

Once this operation has been carried out, the reaction mixture is fed to a distillation column. This column is generally used in processes for the purification of aromatic polyamines and has the aim of separating the desired isomers from those which are of little interest and from the heavy and volatile by-products. Thus, and in the specific case of TDA, the volatile by-products are recovered at the top of the said column with the ortho isomer, the heavy by-products are recovered at the bottom with the meta-TDA.

This column more particularly comprises from 30 to 60 theoretical plates.

It can comprise, without distinction, a stacked packing, rings or trays (perforated trays, valve trays, bubble trays, and the like).

The distillation is generally carried out under vacuum.

It should be noted that the parameters for controlling the distillation column very clearly depend on the nature of the mixture to be treated.

By way of example, the distillation of the mixture comprising the various isomers of TDA and the by-products which accompany it is carried out so that the temperature at the bottom of the column is of the order of 180 to 220° C.

As for the pressure at the column top, still in the case of the abovementioned mixtures comprising TDA, the pressure is, for example, of the order of from 3 to 120 kPa.

The mixture to be treated is advantageously fed in the form of a liquid stream.

The level for the introduction of the stream into the column can be determined in the usual way by a person skilled in the art. However, by way of example, this stream is fed in the second third of the column.

The volatile by-products as well as the isomers with the lowest boiling points (ortho-TDA) are conventionally recovered at the top of this column.

A liquid stream, known as the first stream, is recovered at the column bottom, which stream comprises the heavy by-products with the isomers with the highest boiling points (i.e., the meta-TDAs).

This first stream is advantageously used directly, that is to say without being subjected to a further purification stage, in a subsequent chemical reaction, such as, for example, phosgenation.

The first alternative form according to the invention consists in drawing off from the side, in the bottom third of the column, a stream (known as the second stream (i)), which is more particularly in the gaseous form. The withdrawal preferably takes place above the boiler and more particularly 1 to 3 trays above the boiler.

This second stream (i) comprises the desired isomers devoid of heavy by-products. It is in an advantageous way simply condensed in an appropriate device and is then, if necessary, stored.

According to this alternative form, this second stream (i) represents at most 20% of the total volume or more than 80% of the total volume. It should be noted that the term "total volume" is understood to denote, in the case of the first alternative form, the stream composed of that recovered at the column bottom (first stream) and that drawn off from the side (second stream (i)).

More particularly, the second stream (i) represents from 0 exclusive to 20% of the total volume or else from 80 to 99% of the total volume.

The second stream (i) preferably represents at most 20% of the total volume, preferably from 1 to 20% of the total volume.

The second alternative form of the invention consists no longer in drawing off a stream from the side but in separating a fraction of the stream recovered at the column bottom (i.e., the first stream), which therefore comprises the heavy by-products as well as the meta-TDA.

In the case of this second alternative form, the separated fraction, corresponding to the second stream (ii), represents from 2 to 50% of the first stream. This fraction advantageously represents 5 to 30% of the first stream.

This second stream (ii) is subsequently partially evaporated.

According to a specific embodiment of the invention, the evaporated portion represents at most 97% by total volume of the second stream (ii). The evaporated portion preferably represents between 50 and 95% by volume with respect to the same reference.

This operation takes place in any type of suitable equipment, such as a boiler or a wiped film evaporator.

This operation generally takes place under vacuum. The evaporation can be carried out under a pressure similar to that of the column.

As the degree of evaporation sought for the meta-TDA is not maximum, it should be noted that, advantageously, it is unnecessary to employ very low pressures. Thus, pressures of the order of 6 to 100 kPa are suitable.

The temperature will depend, on the one hand, on the compounds to be recovered, as well as on the degree of evaporation desired. A person skilled in the art is in a position to adjust these processing conditions.

The evaporated fraction, which is devoid of heavy by-products, is subsequently condensed before being stored, if necessary.

The fraction remaining liquid is returned to the distillation column.

It should be noted that this liquid stream can return directly to the distillation column. According to this possibility, the stream is introduced into the column in the bottom third of the column and preferably at the level of the boiler or else 1 to 2 theoretical plates above the latter. It is this possibility which is represented in FIG. 2.

According to another possibility, which is not represented in FIG. 2, this liquid stream is mixed or introduced at the same level as that introduced initially into the column, in other words the reaction mixture resulting from the hydrogenation, which has been subjected beforehand to dehydration and optionally removal of the solvent, if it had been present during the reaction.

It is likewise possible to mix this liquid stream with that recovered at the column bottom after the splitting which gives the second stream (ii).

What is claimed is:

1. A process for the purification of a mixture of aromatic polyamines obtained by hydrogenation of corresponding aromatic polynitro compounds, said mixture comprising isomers of said amines as well as reaction by-products, comprising the steps of:

a) carrying out a distillation of the mixture in a distillation column wherein a stream of volatile by-products are recovered at the top of the column, b) at the bottom of the column, recovering and separating, a first steam, comprising heavy products and isomers will highest boiling points, c) separating a second stream corresponding to a fraction of the first stream, this fraction representing 2 to 50% of the volume of the first stream, and partially evaporating said second stream to obtain an evaporated portion comprising the isomers with highest boiling points, and a non-evaporated portion, the fraction of the first stream that is not separated as the second stream being used in a phosgenation reaction, d) recovering and recycling the non-evaporated portion in the distillation column, and e) recovering the evaporated portion.

2. A process according to claim 1, wherein the second stream represents from 5 to 30% of the volume of the first stream.

3. A process according to claim 1, wherein the evaporated portion represents at most 97% by total volume of the second stream.

4. A process according to claim 3, wherein the evaporated portion represents between 50 and 95% by volume.

5. A process according to claim 1, wherein partial evaporation in step c) is carried out under a pressure of between 6 and 100 kPa.

6. A process according to claim 5, wherein step e) comprises condensing the evaporated portion.

7. A process according to claim 1, wherein:

the isomers of the aromatic polyamines comprises ortho-toluenediamine and meta-toluenediamine, in step a), the stream recovered at the too of the column comprises ortho-toluenediamine and volatile by-products, in step b), the first stream comprises heavy products and meta-toluenediamine as an isomers with highest boiling point, in step c), the isomer with highest boiling point is meta-toluenediamine, and the fraction of the first stream that is not separated as the second stream comprises heavy products and meta-toluenediamine, and in step e), the recovered evaporated portion comprises meta-toluenediamine.

8. A process for the purification of a mixture of aromatic polyamines obtained by hydrogenation of corresponding aromatic polynitro compounds, said mixture comprising isomers of said amines as well as reaction by-products, comprising the steps of:
- a) carrying out a distillation of the mixture in a distillation column wherein a stream of volatile by-products are recovered at the top of the column,
- b) at the bottom of the column, recovering and separating, a first stream, comprising heavy products and isomers with highest boiling points, and use it in a phosgenation reaction,
- c) separating a second stream corresponding to a stream drawn off in gas phase from a side, and in a lower third of said column, comprising the isomers with highest boiling point, this stream representing at most 20% or more than 80% of the total volume of said first and second stream, and
- d) recovering the second stream.

9. A process according to claim 8, wherein the second stream represents from 0 exclusive to 20% of the total volume of first and second stream or from more than 80 to 99% of the total volume of first and second stream.

10. A process according to claim 9, wherein step d) comprises condensing the second stream.

11. A process according to claim 8, wherein the isomers of the aromatic polyamines comprises ortho-toluenediamine and meta-toluenediamine, in step a), the stream recovered at the top of the column comprises ortho-toluenediamine and volatile by-products, in step b), the first steam comprises heavy products and meta-toluenediamine as an isomers with highest boiling point, in step c), the isomer with highest boiling point is meta-toluenediamine, and in step d), the recovered second stream comprises meta-toluenediamine.

\* \* \* \* \*